United States Patent [19]
Niznick et al.

[11] Patent Number: 5,575,650
[45] Date of Patent: Nov. 19, 1996

[54] CUTTING DRILL FOR ENDOSSEOUS IMPLANTS

[75] Inventors: Gerald A. Niznick, Las Vegas, Nev.; Ines A. Traverse, Moorpark, Calif.

[73] Assignee: Core-Vent Corporation, Las Vegas, Nev.

[21] Appl. No.: 398,118

[22] Filed: Mar. 3, 1995

[51] Int. Cl.⁶ ........................................ A61C 3/02
[52] U.S. Cl. .......................................... 433/165; 408/224
[58] Field of Search ...................... 433/172, 173, 433/165, 166; 408/224, 225, 58, 59

[56] References Cited

U.S. PATENT DOCUMENTS

| 4,021,920 | 5/1977 | Kirschner et al. ............... 433/165 X |
| 4,345,899 | 8/1982 | Vlock ................................ 433/165 |
| 4,605,347 | 8/1986 | Jodock et al. ..................... 408/224 |
| 4,820,156 | 4/1989 | Ross .................................. 433/165 |
| 4,936,721 | 6/1990 | Meyer ............................... 408/224 |
| 5,173,014 | 12/1992 | Agapiou et al. .................. 408/59 |
| 5,261,818 | 11/1993 | Shaw ................................. 433/165 |
| 5,429,504 | 7/1995 | Peltier et al. ..................... 433/165 |

FOREIGN PATENT DOCUMENTS

| 3433570 | 3/1986 | Germany ........................... 433/165 |
| 6038987 | 2/1994 | Japan ................................ 433/165 |

Primary Examiner—Nicholas D. Lucchesi

[57] ABSTRACT

A twist-bladed dental drill with an enhanced cutting tip for preparing surgical sites for endosseous implants includes a central, axially-extending internal passageway for carrying fluid through the shank of the drill to the outer surfaces of the drill.

9 Claims, 2 Drawing Sheets

CUTTING DRILL FOR ENDOSSEOUS IMPLANTS

This invention relates to instruments, particularly dental drills, used for preparing surgical sites in endosseous structures in human subjects. More particularly, the invention relates to dental drills for endosseous implant procedures. This invention relates to the subject matter disclosed and claimed in U.S. patent application Ser. No. 08/269,598, filed Jul. 1, 1994 in the U.S. Patent & Trademark Office, and entitled "ENHANCED CUTTING DRILL TIP FOR ENDOSSEOUS IMPLANTS". The entire text of that application, including drawings and claims as filed in the U.S. Patent & Trademark Office on Jul. 1, 1994, are incorporated herein by this reference as though fully set forth here.

The dental drills of this invention are especially useful for enhanced cutting in bone and in preparing surgical sites for endosseous implants in the jawbones of human subjects. These drills comprise a generally-cylindrical body (or shank) with a plurality of helical grooves along a substantial portion of the length of this shank. The drills terminate in a cutting tip that has primary and, in some embodiments, primary and secondary cutting edges. The generally-cylindrical shank preferably has internal fluid passageways, preferably along its central axis, that exit near the cutting tip and that discharge fluid onto that tip when the drill is in use. In preferred embodiments, the helical grooves formed along the cylindrical shank extend longitudinally along the shank's lateral surfaces and terminate in a cutting tip at the distal end of the drill.

In preferred embodiments, these new drills include a central axial fluid passageway with radially-projecting exit bores near the tip of the drill that deliver fluid, such as water, to desired drill surfaces including, but not limited to, the tip of the drill.

These new drills have, at the tip, a positive rake angle. In some embodiments, these drills can have split points at the tip of each blade, forming secondary cutting flutes or edges. These secondary cutting flutes are offset from the primary cutting flutes and, together with the primary cutting flutes, allow chips from the drilling to break into smaller pieces, facilitating their ejection from the drilling site. An optimal point angle in conjunction with a positive rake angle split point decreases the torque needed for drilling.

DETAILED DESCRIPTION OF THE DRAWINGS

Figure 1:
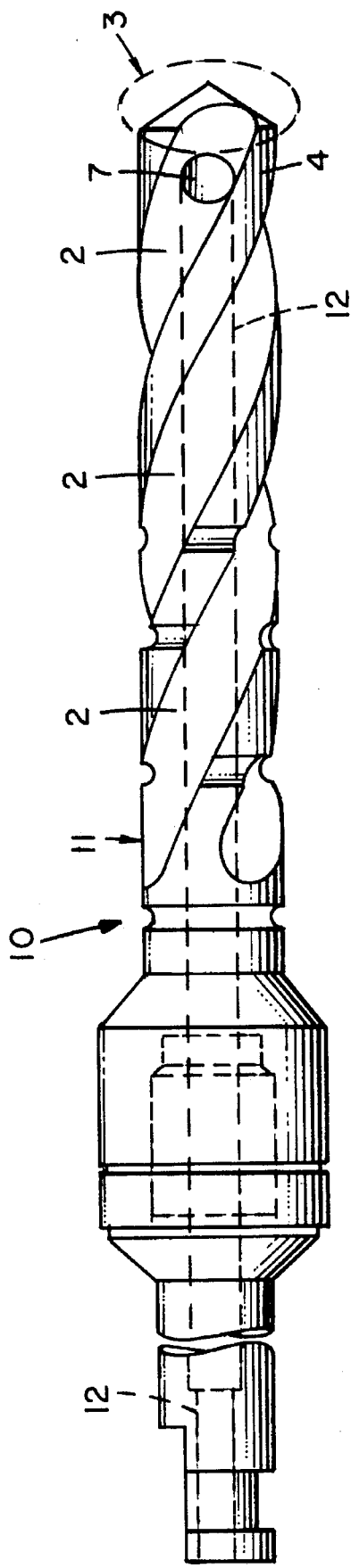
FIG. 1 is a side elevation view of one embodiment of the twist drill of this invention.

FIG. 1 shows a preferred embodiment of the irrigated twist drill 10 of this invention. Drill shank 11 includes spiral-shaped grooves 2 that form three twisted blades along the longitudinal, lateral surfaces of drill shank 11.

Drill 10 includes an internal passageway 12 for irrigating portions of the drill during operation, including at the cutting tip 3, or intermediate points along shaft 11, as desired. Fluid passageway 12 in combination with fluid discharge orifice 7 at cutting tip 3 delivers fluid such as water to tip 3 of drill 10, and to the lateral surfaces of the drill as well.

Figure 2:
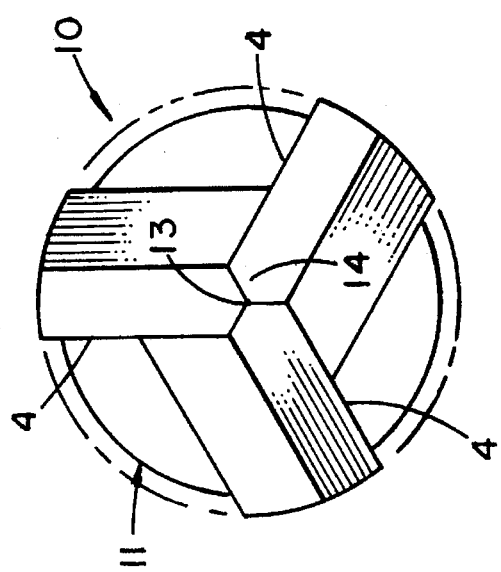
FIG. 2 is a distal end view of a first embodiment of the drill blade cutting tip.
Figure 3:
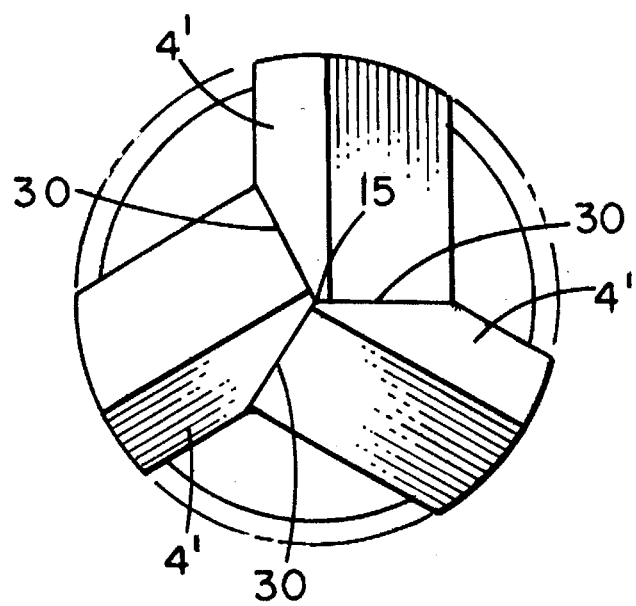
FIG. 3 is a distal end view of a second embodiment of the drill blade cutting tip.
Figure 4:
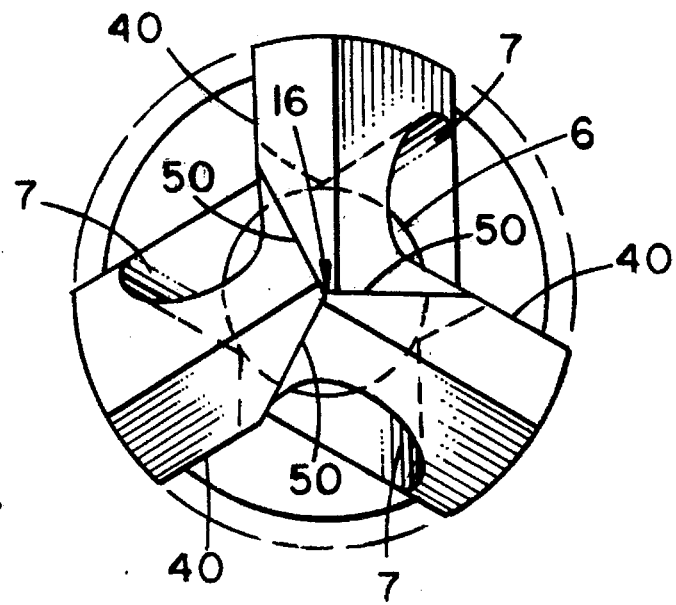
FIG. 4 is a distal end view of a third embodiment of the drill blade cutting tip.

FIGS. 2, 3 and 4 show different embodiments of cutting tip 3 of the drill.

FIG. 2 shows three twist blades 4 coming together to form blade tip 13 and web 14.

FIG. 3 shows three twist blades 4' coming together at the tip to form point 15, primary cutting edges 4', and secondary cutting edges FIG. 4 shows three twist blades coming together to form drill point 16, and three primary cutting edges 40, three secondary cutting edges 50, and fluid discharge orifice 7 for fluid passage 6.

The second and third tip embodiment shown in FIGS. 3 and 4, respectively, each include a split point that forms three primary and three secondary cutting flutes with the secondary flutes offset with respect to the primary cutting flutes. This offset, as bone is penetrated by the drill, causes bone chips in the drill site to be broken into smaller chips, facilitating their ejection from the drilling site.

In preferred embodiments, the secondary cutting flutes are enhanced by incorporation of a positive rake angle into each split point. This rake angle is typically in the range of about 10 degrees to about 15 degrees with reference to the plane of relief cut into each plane. The degree of rake depends upon the material being drilled and the characteristics of the drill bit material.

Though the embodiments shown in the drawings include three twisted blades, the drill could have any number of blades, e.g. 2–6. In preferred embodiments, the diameter of the drill is in the range of about 2 millimeters to about 5 millimeters.

What is claimed is:

1. A dental drill for use in drilling an opening in human jawbone tissue comprises:

a cylindrical shank with a proximal end, a distal end, and external lateral surfaces, said shank having an internal passageway for delivering a liquid to said lateral surfaces, said drill also comprising a plurality of cutting blades extending helically around said lateral surfaces and terminating at the distal end of the drill in a cutting point converging upon the center axis of said drill, each of said blades having a primary cutting flute with a relief on its trailing edge, and a secondary cutting flute formed by a split point having a positive rake angle, said split point converging on the center axis of the drill, said secondary cutting flute being offset with respect to said primary cutting flute, precluding chisel edges on said cutting blades.

2. The drill of claim 1 wherein said split point comprises a positive rake angle with respect to a trailing edge of each of said blades.

3. The drill of claim 1 wherein said positive rake angle is in the range of about 10° to about 15°.

4. The drill of claim 1 comprising three blades and three slit points.

5. A dental drill for use in drilling an opening in human jawbone tissue for receiving an endosseous dental implant, comprising a cylindrical shank with a plurality of twisted blades extending helically around the lateral surfaces of said shank, each blade comprising a primary cutting flute and a split point converging to the center axis of the drill, said split point forming a secondary cutting flute, offset with respect to said primary cutting flute, precluding chisel edges on said cutting blades.

6. The drill of claim 5 wherein said split point comprises a positive rake angle with respect to a trailing edge of each of said blades.

7. The drill of claim 6 wherein said positive rake angle is in the range of about 10° to about 15°.

8. The drill of claim 5 comprising three blades and three split points.

9. A method of using a dental drill for forming openings in the jawbones of patients to receive endosseous dental implants, comprising:

selecting a dental drill including a plurality of twisted blades on the lateral walls of a cylindrical shank, each blade comprising a primary cutting flute and a split point converging to the center axis of said drill, precluding a chisel edge on any of said blades, said split point forming a secondary cutting flute, offset with respect to said primary cutting flute; and utilizing said dental drill to form said openings.

* * * * *